United States Patent [19]

Brown

[11] Patent Number: 5,153,357
[45] Date of Patent: Oct. 6, 1992

[54] PREPARATION OF TRISUBSTITUTED BENZOIC ACIDS AND INTERMEDIATES

[75] Inventor: Richard W. Brown, Richmond, Calif.

[73] Assignee: Imperical Chemical Industries PLC, London, Great Britain

[21] Appl. No.: 809,563

[22] Filed: Dec. 17, 1991

Related U.S. Application Data

[62] Division of Ser. No. 650,337, Feb. 4, 1991, Pat. No. 5,101,065.

[51] Int. Cl.$^5$ .............................................. C07C 67/14
[52] U.S. Cl. ................................ 560/142; 562/429; 562/432; 562/840; 562/31; 562/43
[58] Field of Search ........................................ 560/142

[56] References Cited

U.S. PATENT DOCUMENTS 4,327,224  4/1982  Archer .................................. 560/142
4,814,110  3/1989  Fong et al. ...................... 560/142 X
4,898,973  2/1990  Lee ....................................... 562/429

*Primary Examiner*—José Dees
*Assistant Examiner*—Vera C. Clarke
*Attorney, Agent, or Firm*—Michael J. Bradley; Edwin H. Baker

[57] ABSTRACT

A process for the preparation of 2-(hydrogen, halogen or lower alkyl)-3-(hydroxy, $C_1$–$C_4$ alkoxy, $C_1$–$C_4$ haloalkoxy, —$OCH_2CH_2OCH_3$, —$OCH_2CH_2OC_2H_5$, —$OCH_2CH_2SCH_3$ or —$OCH_2CH_2SC_2H_5$)-4-(alkylthio or alkylsulfonyl)-acetophenones.

3 Claims, No Drawings

PREPARATION OF TRISUBSTITUTED BENZOIC ACIDS AND INTERMEDIATES

This is a division of application Ser. No. 07/650,337, filed Feb. 4, 1991, now U.S. Pat. No. 5,101,065.

BACKGROUND OF THE INVENTION

Certain 2-(2′,3′,4′-trisubstituted benzoyl)-1,3-cyclohexanedione herbicides are described in U.S. Pat. No. 4,780,127, issued Oct. 25, 1988; U.S. Pat. No. 4,816,066, issued Mar. 28, 1989; and PCT International Publication No. WO 90/05712, published May 31, 1990 and entitled Certain 2-(2′,3′,4′-trisubstituted benzoyl)-1,3-cyclohexanediones, with William J. Michaely, inventor and all incorporated herein by reference.

The above-described herbicidal compounds can have the following structural formula

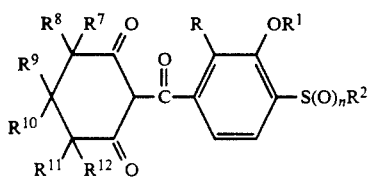

wherein R is hydrogen, halogen or alkyl; $R^7$ through $R^{12}$ are hydrogen or $C_1$–$C_4$ alkyl or $R^7$, $R^8$, $R^{11}$ and $R^{12}$ are methyl and $R^9$ and $R^{10}$ together are carbonyl; $R^1$ is $C_1$–$C_4$ alkyl, $C_1$–$C_4$ haloalkyl, —$CH_2CH_2OCH_3$, —$CH_2CH_2OC_2H_5$, —$CH_2CH_2SCH_3$, or —$CH_2CH_2SC_2H_5$; $R^2$ is $C_1$–$C_4$ alkyl; and n is the integer 0 or 2.

These herbicides can be prepared by reacting a dione of the structural formula

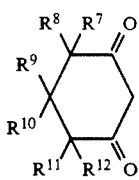

wherein $R^7$ through $R^{12}$ are as defined with a mole of trisubstituted benzoyl chloride of the structural formula

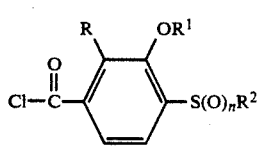

wherein n, R, $R^1$ and $R^2$ are as defined above.

This invention relates to a process for the preparation of 2-(hydrogen, halogen or lower alkyl)-3-(hydroxy, $C_1$–$C_4$ alkoxy, $C_1$–$C_4$ haloalkoxy, —$OCH_2CH_2OCH_3$, —$OCH_2CH_2OC_2H_5$, —$OCH_2CH_2SCH_3$ or —$OCH_2CH_2SC_2H_5$)-4-(alkylthio or alkylsulfonyl)-acetophenones and to the intermediates prepared by the process.

SUMMARY OF THE INVENTION

One embodiment of this invention is directed to a process for the preparation of 2-(hydrogen, halogen or lower alkyl)-3-(hydroxy, $C_1$–$C_4$ alkoxy, $C_1$–$C_4$ haloalkoxy, —$OCH_2CH_2OCH_3$, —$OCH_2CH_2OC_2H_5$, —$OCH_2CH_2SCH_3$ or —$OCH_2CH_2SC_2H_5$)-4-(alkylthio or alkylsulfonyl)-acetophenones represented by the following reaction steps:

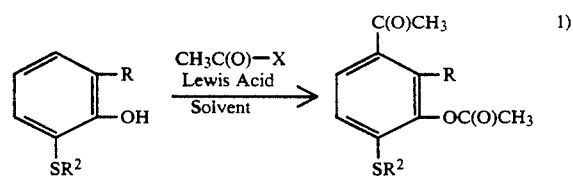

wherein R is hydrogen, halogen or $C_1$–$C_2$ alkyl; $R^2$ is $C_1$–$C_4$ alkyl; and X is halogen

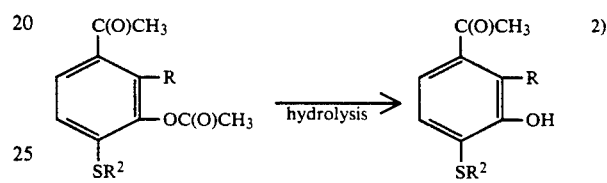

wherein R is hydrogen, halogen or $C_1$–$C_2$ alkyl; and $R^2$ is $C_1$–$C_4$ alkyl

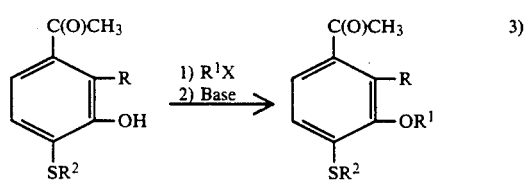

wherein R is hydrogen, halogen or $C_1$–$C_2$ alkyl; $R^1$ is $C_1$–$C_4$ alkyl, $C_1$–$C_4$ haloalkyl, —$CH_2CH_2OCH_3$, —$CH_2CH_2OC_2H_5$, —$CH_2CH_2SCH_3$, or —$CH_2CH_2SC_2H_5$; and $R^2$ is $C_1$–$C_4$ alkyl

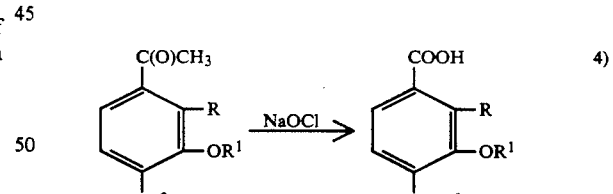

wherein R, $R^1$ and $R^2$ are as defined in step 3

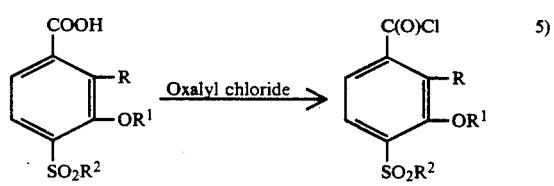

wherein R, $R^1$ and $R^2$ are as defined in step 3 or in the alternative, the acetyl and alkylthio ring groups can be oxidized sequentially as follows:

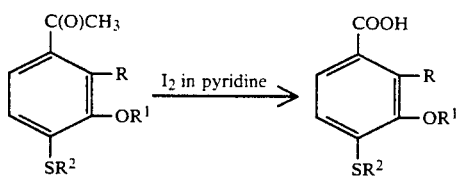

wherein R, R$^1$ and R$^2$ are as defined in step 3

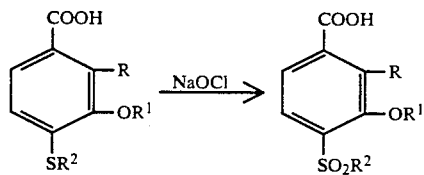

wherein R, R$^1$ and R$^2$ are as defined in step 3 or in the alternative, the alkylthio and acetyl ring groups can be oxidized sequentially as follows:

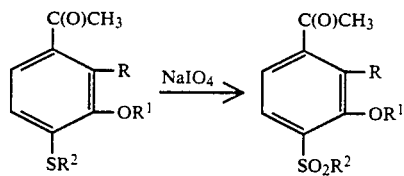

wherein R, R$^1$ and R$^2$ are as defined in step 3

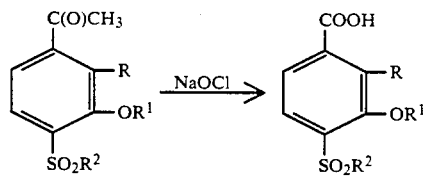

wherein R, R$^1$ and R$^2$ are as defined in step 3.

Another embodiment of this invention is the intermediate reaction product of Reaction step 1. These trisubstituted acetophenones have the structural formula

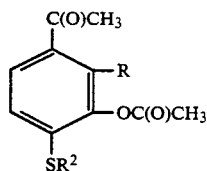

wherein R is hydrogen; halogen, preferably chlorine; or C$_1$-C$_2$ alkyl, preferably methyl, most preferably chlorine and R$^2$ is C$_1$-C$_4$ alkyl, preferably methyl or ethyl, most preferably ethyl.

Still another embodiment of this invention is the intermediate reaction product of Reaction step 2. These intermediate compounds have the structural formula

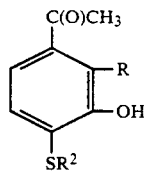

wherein R is hydrogen; halogen, preferably chlorine; or C$_1$-C$_2$ alkyl, preferably methyl, most preferably chlorine and R$_2$ is C$_1$-C$_4$ alkyl, preferably methyl or ethyl, most preferably ethyl.

And another embodiment of this invention is the intermediate reaction product of Reaction step 3. These intermediate compounds have the structural formula

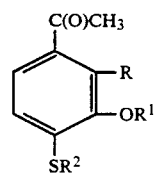

wherein R is hydrogen; halogen, preferably chlorine; or C$_1$-C$_2$ alkyl, preferably methyl, most preferably chlorine, R$^1$ is C$_1$-C$_4$ alkyl, C$_1$-C$_4$ haloalkyl, —CH$_2$CH$_2$OCH$_3$, —CH$_2$CH$_2$OC$_2$H$_5$, —CH$_2$CH$_2$SCH$_3$, or —CH$_2$CH$_2$SC$_2$H$_5$; and R$^2$ is C$_1$-C$_4$ alkyl, preferably methyl or ethyl, most preferably ethyl.

Yet another embodiment of this invention are the intermediate compounds that are the reaction product of Reaction step 4c. These intermediates have the structural formula

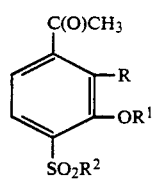

wherein R is hydrogen; halogen, preferably chlorine; or C$_1$-C$_2$ alkyl, preferably methyl, most preferably chlorine, R$_1$ is C$_1$-C$_4$ alkyl, C$_1$-C$_4$ haloalkyl, —CH$_2$CH$_2$OCH$_3$, —CH$_2$CH$_2$OC$_2$H$_5$, —CH$_2$CH$_2$SCH$_3$, or —CH$_2$CH$_2$SC$_2$H$_5$; and R$^2$ is C$_1$-C$_4$ alkyl, preferably methyl or ethyl, most preferably ethyl.

DETAILED DESCRIPTION OF THE INVENTION

Referring to the five reaction steps under the "Summary of the Invention" section, this invention can be understood by considering the following detailed description.

The process of this invention is depicted by Reaction step 1. Reaction steps 2 through 5 are provided to illustrate process steps for the preparation of the 2,3,4-trisubstituted benzoyl chloride reaction product of Reaction step 5 which has known utility in the preparation of herbicidal compounds. Also, the intermediate reaction products of Reaction steps 1, 2, 3, and 4c are embodiments of this invention.

In Reaction step 1, a mole of the phenol is reacted with a mole of the Lewis acid to form a first complex.

Using aluminum chloride as the Lewis acid, the first complex has the structural formula

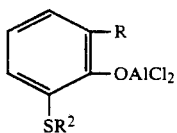

wherein R and R² are as defined.

Preferably, an additional mole or more of the Lewis acid is added to the reaction mixture but remains unreacted. Next, two moles of the acetyl halide is added to the reaction mixture. A mole of the acetyl halide reacts with a mole of the Lewis acid to form a second complex. When aluminum chloride is the Lewis acid, the complex has the structural formula

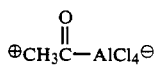

This second complex is an acylating agent and reacts with the first complex to add an acetyl group to the phenol para to the alkyl thio group as shown in Reaction step 1.

The second mole of the acetyl halide acylates the phenolic oxygen to form the acetoxy group ortho to the alkyl thio group on the ring as shown in Reaction step 1.

Thus in Reaction step 1, a mole of the phenol is mixed with a minimum of two moles of the acetyl halide, preferably acetyl chloride and a minimum of two moles of a Lewis acid, preferably aluminum chloride. The Lewis acid serves as a catalyst in the reaction. Preferably the reaction is run in an halogenated solvent such as ethylene dichloride, chloroform, or dichloromethane. The reaction can be run at a temperature of about 0° C. to about reflux temperature. Preferably, the reaction is run at about 20° C. to about 50° C.

At least one mole of the Lewis acid must be mixed with the phenol for a sufficient time to form the first complex of the Lewis acid and the hydroxyl group of the phenol before the acetyl halide is brought into contact with the phenol in the reaction mixture. The mixing can be done at room temperature, although lower and higher temperatures are also operative. If a mole of the phenol and at least one mole of the Lewis acid are mixed before contact with the acetyl halide, then the desired 2, 3, 4-trisubstituted acetophenone reaction product is obtained in high purity. Without this mixing, the acetyl substitution occurs para to the hydroxy group of the phenol, thus forming an undesired isomer of the desired 2, 3, 4-trisubstituted acetophenone. The preparation of the desired 2, 3, 4-trisubstituted acetophenone compound is surprising in view of the prior art. For example, U.S. Pat. No. 4,327,224 teaches that reaction of O-(methylthio) phenol with acetyl chloride and aluminum chloride in nitrobenzene affords the isomeric 4'-hydroxy-3'-(methylthio) acetophenone.

The desired reaction product can be recovered by conventional techniques such as by diluting the reaction mixture with additional solvent and pouring the diluted mixture into ice water. The aqueous phase is extracted with additional solvent and the combined organic phases are washed with dilute hydrochloric acid, dried and then concentrated in vacuo to give the desired acetophenone in high yield and in high purity.

Reaction step 2 is a simple hydrolysis step and can be carried out by any of the methods described by E. Haslam on p. 172 of "Protective Groups in Organic Chemistry", J. F. W. McOmie, Ed., 1973. Typically, the reaction is carried out by reacting a molar amount of the acetophenone of Reaction step 1 with at least a mole of a base such as sodium hydroxide optionally in a solvent such as water or methanol or a combination of the two with heating at about 50° C. to about 100° C. for about an hour. The resulting solution is cooled and acidified to pH 1 with hydrochloric acid. The resulting precipitated solids are collected by filtration to yield the desired product in high yields (greater than 95%).

For Reaction step 3, one mole of the substituted acetophenone reaction product of step 2 is reacted with an appropriate alkylating agent such as a 2-chloroethyl ethyl ether, 2-chloroethyl methyl ether, 2-chloroethyl methyl sulfide, 2-chloroethyl ethyl sulfide or $C_1$-$C_4$ alkyl chloride along with a catalytic amount of potassium iodide and a molar excess of a base such as potassium carbonate. Alkyl iodides such as methyl iodide or ethyl iodide may also be used. In these cases, the catalytic potassium iodide is not needed and little or no heat is required. The reaction is run at 25° C. to 80° C. for 4 hours with agitation. The novel intermediate reaction product is recovered by conventional techniques.

For Reaction step 4, the novel intermediate compounds, 4-($C_1$-$C_4$-alkylsulfonyl)-2,3-disubstituted benzoic acid compounds can be prepared by oxidizing a molar amount of the 4-($C_1$-$C_4$-alkylthio)-2,3-disubstituted acetophenone prepared in Reaction step 3 with at least 5 moles of an oxidizing agent such as sodium hypochlorite in a suitable solvent such as dioxane by heating a solution of the reactants to 80° C. After an exothermic reaction, the mixture is cooled and acidified with hydrochloric acid. The desired intermediate which is a precipitate is recovered by filtration.

In Reaction step 5, the trisubstituted benzoic acid product of Reaction step 4 is converted to its acid chloride by reaction with oxalyl chloride according to the teaching of Reagents for Organic Synthesis, Vol. 1, L. F. Fieser and M. Fieser, pp. 767–769 (1967).

Reaction step 4a is run by reacting the substituted acetophenone with a mole excess of iodine in pyridine at a temperature of about 50° C. to about 100° C., followed by hydrolysis with sodium hydroxide in the manner described by L. C. King, *J. Amer. Chem. Soc.*. 66, 894 (1944). The desired intermediate compound is recovered by conventional techniques.

Reaction step 4b is run by reacting the described 2,3-disubstituted-4-($C_1C_4$ alkylthio) benzoic acid with a molar excess of an oxidizing agent such as sodium hypochlorite in a suitable solvent such as dioxane by heating the solution to a temperature between 50° C. and 100° C. After the reaction, the mixture is cooled and acidified with hydrochloric acid. The desired intermediate product, which is a precipitate, is recovered by filtration.

Reaction step 4c is run by reacting the substituted acetophenone from Reaction step 3 with at least 2 moles of an oxidizing agent such as sodium iodate, $NaIO_4$, in an aqueous solvent at reflux temperature. The reaction product is recovered by conventional techniques.

Reaction step 4d is run by reacting the substituted acetophenone from Reaction step 4c with at least three moles of an oxidizing agent such as sodium hypochlorite in a suitable solvent such as dioxane by heating the solution to a temperature between 50° C. and 100° C. After the reaction, the mixture is cooled and acidified with hydrochloric acid. The desired intermediate product, which is a precipitate, is recovered by filtration.

EXAMPLE I 3-acetoxy-4-(ethylthio) acetophenone

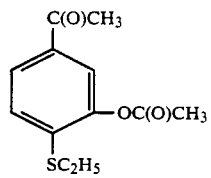

A mixture of 5.0 g of 2-(ethylthio)phenol and 10.6 g of aluminum chloride in 20 ml of dichloromethane was stirred at ambient temperature for 30 min. Acetyl chloride (5.7 ml) was added dropwise over 25 min. and the resulting solution stirred at ambient temperature for 1 hr. The reaction mixture was diluted with dichloromethane and poured into 100 ml of ice water. The aqueous phase was extracted with dichloromethane and the combined organic phases washed with dilute hydrochloric acid, dried, and concentrated in vacuo to afford 7.1 g (94% yield) of 3-acetoxy-4-(ethylthio)acetophenone.

EXAMPLE II

3-Hydroxy-4-(ethylthio)acetophenone

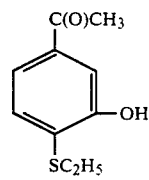

A solution of 7.0 g of 3-acetoxy-4-(ethylthio)acetophenone, 44 ml of 5% sodium hydroxide solution, and 10 ml of methanol was heated at 75° C. for 1 hr. The cooled solution was acidified to pH 1 with 3 molar (M) HCl, and the resulting solids collected by filtration to give 5.6 g (96% yield) of the desired product 3-hydroxy-4-(ethylthio)acetophenone, mp 108°–109° C.

EXAMPLE III

2-Chloro-3-acetoxy-4-(ethylthio)acetophenone

A mixture of 1.8 g of 2-chloro-6-(ethylthio)phenol and 3.1 g of aluminum chloride in 15 ml of 1,2-dichloroethane was stirred at ambient temperature for 30 minutes. Acetyl chloride (1.7 ml) was added dropwise over a 5 minute period and the resulting solution was heated at reflux for 1 hour. The reaction mixture was diluted with 1,2-dichloroethane and poured into 50 ml of ice water. The aqueous phase was extracted with 1,2-dichloroethane and the combined organic layers were washed with dilute hydrochloric acid, dried, and concentrated in vacuo to afford 1.1 g (50% yield) of 3-acetoxy-2-chloro-4-(ethylthio)acetophenone.

I claim:

1. A process for preparing a compound having the structural formula

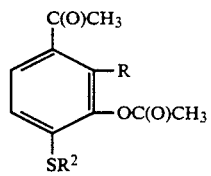

wherein R is hydrogen, halogen or $C_1$–$C_2$ alkyl and $R^2$ is $C_1$–$C_4$ alkyl comprising reacting a mole of a phenol compound having the structural formula

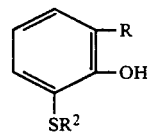

wherein R and $R^2$ are as defined with at least two moles each of acetyl halide and a Lewis acid with the proviso that the phenol and at least one mole of the Lewis acid are reacted to form a complex before the addition of the acetyl halide and any remaining Lewis acid.

2. The process of claim 1 wherein R is chlorine, bromine or methyl, $R^2$ is methyl or ethyl, the acetyl halide is acetyl chloride and the Lewis acid is aluminum chloride.

3. The process of claim 2 wherein R is chlorine and $R^2$ is ethyl.

* * * * *